(12) United States Patent
Kim

(10) Patent No.: US 10,245,446 B2
(45) Date of Patent: Apr. 2, 2019

(54) MARKER-FLANGE FOR MRI-GUIDED BRACHYTHERAPY

(71) Applicant: University of Iowa Research Foundation, Iowa City, IA (US)

(72) Inventor: Yusung Kim, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 564 days.

(21) Appl. No.: 13/826,873

(22) Filed: Mar. 14, 2013

(65) Prior Publication Data
US 2014/0275964 A1    Sep. 18, 2014

(51) Int. Cl.
*A61N 5/10* (2006.01)
*A61B 90/00* (2016.01)

(52) U.S. Cl.
CPC ............ *A61N 5/1007* (2013.01); *A61B 90/39* (2016.02); *A61B 2090/3954* (2016.02); *A61N 5/1016* (2013.01); *A61N 2005/1012* (2013.01)

(58) Field of Classification Search
CPC .... A61B 2019/5454; A61B 2019/5483; A61B 17/42–17/44; A61B 2017/4216; A61B 2019/54; A61B 2019/5433; A61B 19/54–19/56; A61B 2019/5404–2019/568; A61B 90/39; A61B 2090/3933; A61N 2005/1012; A61N 5/1016; A61N 5/1001; A61N 5/1007–5/1027; A61M 31/0005; A61M 25/0108; A61M 25/0105
USPC .................................................. 600/5, 6, 420
See application file for complete search history.

(56) References Cited

U.S. PATENT DOCUMENTS

| 5,012,357 | A | * | 4/1991 | Schoeppel et al. ............. 378/65 |
| 5,469,847 | A | * | 11/1995 | Zinreich et al. ............... 600/414 |
| 6,419,680 | B1 | | 7/2002 | Cosman et al. |
| 6,687,533 | B1 | | 2/2004 | Hirano et al. |

(Continued)

FOREIGN PATENT DOCUMENTS

| EP | 2508907 A1 * | 10/2012 | ............. A61B 5/055 |
| WO | 2009009760 | 1/2009 | |
| WO | 20120125946 | 9/2012 | |

OTHER PUBLICATIONS

J. Schindel, M. Muruganandham, F. Christopher Pigge, J. Anderson, Y. Kim, Magnetic Resonance Imaging (MRI) Markers for MRI-Guided High-Dose-Rate Brachytherapy: Novel Marker-Flange for Cervical Cancer and Marker Catheters for Prostate Cancer, International Journal of Radiation Oncology Biology Physics, vol. 86, Iss. 2, Feb. 20, 2013.*

(Continued)

*Primary Examiner* — Thaddeus B Cox
(74) *Attorney, Agent, or Firm* — Smith, Gambrell & Russell, LLP

(57) ABSTRACT

Disclosed herein is a marker-flange for use with a brachytherapy applicator, having a flange body with a first face, a second face, and a hollow chamber positioned between the first and second faces. A cavity extending through the flange body is dimensioned to receive a tandem in a brachytherapy applicator in a press-fit connection, so as to affix the flange-marker to an outside surface of the tandem. The hollow chamber includes an MR imaging responsive marker agent that provides strong signal intensities and a high geometric accuracy in MR imaging.

22 Claims, 15 Drawing Sheets

(56) References Cited

U.S. PATENT DOCUMENTS

| | | | |
|---|---|---|---|
| 6,975,896 | B2 | 12/2005 | Ehnholm et al. |
| 7,761,138 | B2 | 7/2010 | Wang et al. |
| 2002/0198506 | A1* | 12/2002 | Whalen et al. ............... 604/328 |
| 2006/0173235 | A1* | 8/2006 | Lim et al. ..................... 600/6 |
| 2007/0191707 | A1 | 8/2007 | Denittis |
| 2010/0113912 | A1 | 5/2010 | Traboulsi et al. |
| 2010/0145132 | A1 | 6/2010 | Isham |
| 2010/0254897 | A1 | 10/2010 | Frank et al. |
| 2010/0312096 | A1 | 12/2010 | Guttman et al. |
| 2011/0224478 | A1 | 9/2011 | Hannoun-Levi et al. |
| 2012/0123188 | A1 | 5/2012 | Rahimian |
| 2012/0189221 | A1 | 7/2012 | Inada et al. |
| 2012/0277518 | A1* | 11/2012 | Mick ................... A61N 5/1016 600/6 |
| 2013/0053682 | A1* | 2/2013 | Esthappan et al. ............ 600/411 |
| 2014/0005539 | A1* | 1/2014 | Forster et al. ................ 600/431 |

OTHER PUBLICATIONS

Haack, Soren, et al.; "Applicator Reconstruction in MRI 3D Image-Based Dose Planning of Brachytherapy for Cervical Cancer", Radiotherapy and Oncology; pp. 187-193; Oct. 30, 2008.

Hellebust, Taran Paulsen, et al.; "Recommendations for Gynaecological (GYN) GEC-ESTRO Working Group: Considerations and Pitfalls in Commissioning and Applicator Reconstructions in 3D Image-Based Treatment Planning of Cervix Cancer Brachytherapy"; Radiotherapy and Oncology; pp. 153-160; Jul. 19, 2010.

Kim, Yusung, et al.; "Evaluation of Artifacts and Distortions of Titanium Applicators on 3.0-Tesla MRI: Feasibility of Titanium Applicators in MRI-Guided Brachytherapy for Gynecological Canter"; Int. J. Radiation Oncology Biol. Phys; vol. 80, No. 3; pp. 947-955; 2011.

Kim, Y, et al.; "Feasibility of Source Markers for a Titanium Tandem and Ovoids Applicators in MRI Guided Brachytherapy: Implications of Source Reconstruction on 3 Tesla MR Images"; Brachytherapy 8, 121; 2009.

Perez-Calatayud, J, et al,; "Exclusive MRI-Based Tandem and Colpostats Reconstructions in Gynaecological Brachytherapy Treatment Planning"; Radiother Oncol. 91, 181-186 (2009).

Crooks, I.A.; "A CT- and MRI-Compatible Reference Marker Box for Use with Stereotaxic Frames"; AJR American Journal of Roentgenology 164, 178-180 (1995).

Kim, Y. et al.; "Evaluation of Titanium Applicator Reconstructions Accuracy for Exclusive 3.0 Tesla MRI Guided Brachytherapy for GYN Cancer"; Medical Physics, AAPM (2011).

Rousseau, D. et al.; "Technical Note: Magnetic Resonance Imaging of Agarose Gel Phantom for Assessment of Three-Dimensional Dose Distribution in Linac Radiosurgery"; The British Journal of Radiology 67, 646-648; (1994).

Kim, Y.; et al.; "Evaluation of Artifacts and Distortions of Titanium Applicators on 3.0-Tesla MRI: Feasibility of Titanium Applicators in MRI-Guided Brachytherapy for Gynecological Cancer"; Int. J. Radiat Oncol. Biol. Phy. 247-955 (2011).

* cited by examiner

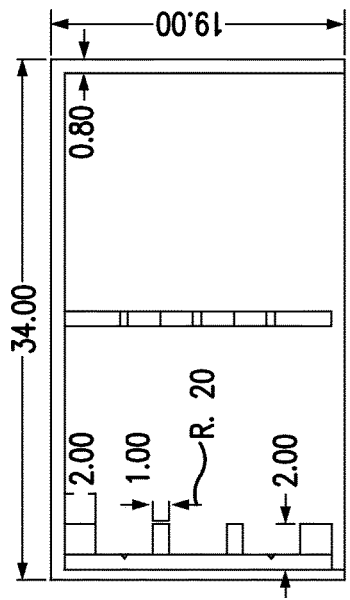
FIG. 5A
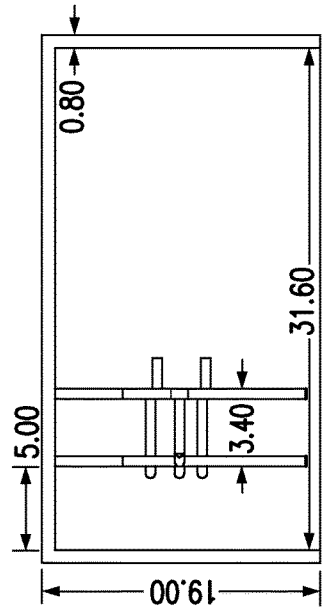
FIG. 5B
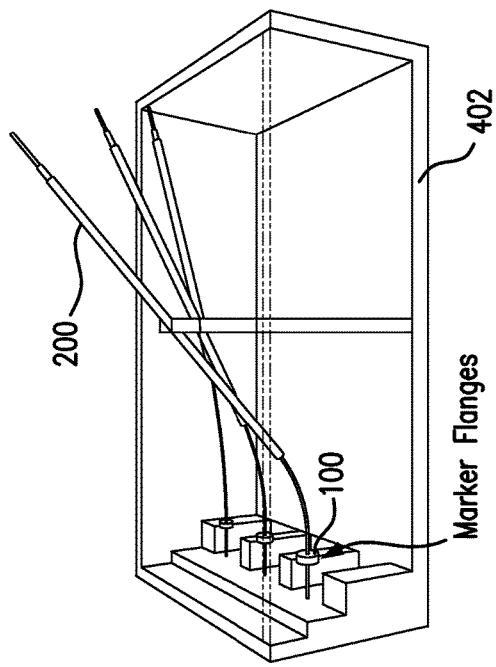
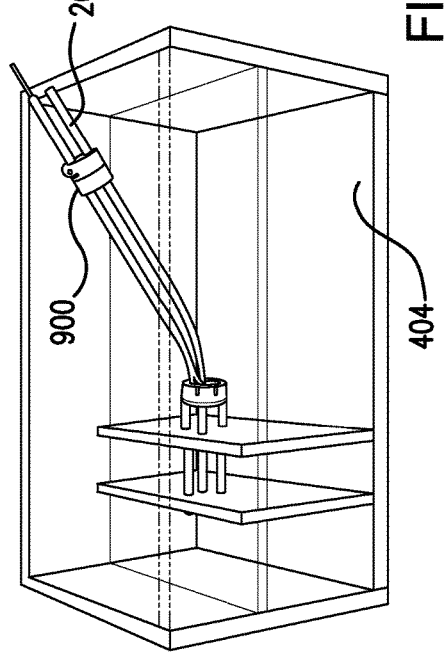

MARKER-FLANGE FOR MRI-GUIDED BRACHYTHERAPY

BACKGROUND OF THE INVENTION

1. Field of the Invention

This invention relates to devices and methods for use in therapeutic treatments. In particular, the present invention relates to a marker-flange for use in Magnetic Resonance Imaging (MRI) guided radiation therapy with a brachytherapy applicator.

2. Description of the Related Art

Brachytherapy (also referred to as "short-distance therapy") is a medical treatment procedure wherein target tissues, such as cancerous tumors, are treated with radiation sources that are placed inside or directly adjacent to the target tissue. Example target tissue includes cervical, vaginal, endometrial, breast, prostate, esophageal, lung, and skin cancers. Example applicators include interstitial needles, intraluminal applicators and intracavitary applicators.

Brachytherapy is a favorable alternative or supplemental treatment to External Beam Radiation Therapy (EBRT). In particular, EBRT procedures are performed by directing a radiation beam at the target tissues within the body from a radiation source external to the body. This normally results in radiation beams passing through healthy tissue before reaching the target tissue. However, by placing a radiation source inside or directly adjacent to the target tissue, brachytherapy procedures are capable of delivering a focused dose of radiation to the target tissue with relatively low dosages of radiation being delivered to surrounding or intervening healthy tissues and nearby organs at risk. Thus, as compared to EBRT procedures, brachytherapy procedures offer an effective manner for treating target tissue with very high radiation doses while presenting less concern for overdosing nearby healthy tissues.

Advances in computer imaging technology have led to the use of three-dimensional imaging systems for guiding the introduction of a brachytherapy applicator, as well as the radiation sources delivered thereby, into a patient's body and toward the target tissue. In the past x-ray based imaging systems, such as computed tomography (CT) imaging, were used to image and reconstruct a three-dimensional model of the applicator and the treatment region (e.g., the target tissues and the surrounding healthy tissues and organs at risk) for use as a guide in inserting and placing the applicator in a position for treatment. In recent years, however, preference has been given to the use of magnetic resonance (MR) imaging. In particular, MR imaging is preferred due to its ability to accurately define soft tissues such as the target tissue and the surrounding healthy tissues and organs at risk (e.g., the cervix, prostate, etc.). CT imaging does not offer the same accuracy in identifying these soft tissues. In addition, unlike CT scanning, MR imaging does not expose tissues to ionizing radiation. MR imaging is thus preferred for brachytherapy treatments, which often require multiple dosing procedures and which would therefore require subjecting the patient to repeated doses of ionized radiation if performed with a CT imaging modality.

One challenge that has arisen with MRI-guided brachytherapy is the three-dimensional reconstruction of brachytherapy applicators. This is significant because the brachytherapy applicator represents the irradiation source pathway, thereby defining the regions that will be exposed to radiation doses during treatment. Applicator reconstruction inaccuracies lead to uncertainties in the delivery of radiation doses to both the target tissue and organs-at-risk. Even relatively small geometric uncertainties in the three-dimensional reconstruction of the brachytherapy applicator, in both its dimensions and its placement within the treatment region, may have a critical effect on the radiation doses delivered to the target tissue and organs-at-risk. In particular, a mispositioning of the applicator may result in one or both of an underdosage to the target tissue (leading to the recurrence of the cancerous tissue) and the overdosage of nearby healthy tissue (causing undesired damage of healthy tissues). Accuracy in the positioning of the applicator is paramount as it has been estimated that the radiation dose gradient in an intracavitary brachytherapy application (e.g., gynecological, prostate, etc.) can be as much as 5-12% per millimeter. T. P. Hellebust, et al., Recommendations from Gynecological (GYN) GEC-ESTRO Working group: considerations and pitfalls in commissioning and applicator reconstruction in 3D image-based treatment planning of cervix cancer brachytherapy, Radiotherapy and oncology: journal of the European Society for Therapeutic Radiology and Oncology 96, 153-160 (2010).

In the past, with x-ray based imaging modalities (e.g., CT imaging), brachytherapy procedures were performed with titanium applicators owing to the strength, durability and biocompatibility of the material. However, titanium has been found to generate substantial imaging artifacts when imaged under an MR imaging modality. These artifacts result in an increased uncertainty when attempting to reconstruct a three-dimensional model of a titanium applicator, in both its geometric dimensions and location within the treatment region. As such, current brachytherapy procedures are regularly performed with plastic applicators.

Procedures using plastic applicators are generally performed by inserting a dummy-marker catheter into the plastic applicator. The dummy-marker catheter contains a marker agent that is responsive to MR imaging, in that it is capable of generating a signal sufficient to be observed with MR imaging and used to reconstruct a three-dimensional model of the plastic applicator. The plastic applicator, with the dummy-marker catheter, is then guided during insertion into the treatment region with MR imaging. Once the plastic applicator is in place, the dummy-marker catheter is removed and the applicator is connected to an afterloader that controls the delivery of an irradiation source through the inserted brachytherapy applicator.

However, plastic brachytherapy applicators are not ideal. Plastic applicators generally have an outer diameter of 6-7 mm, which is almost twice the size of a titanium applicator, which generally has an outer diameter of 3-3.2 mm. This increased size of the plastic applicator results in an increased discomfort to patients upon insertion into sensitive regions of the body (e.g., the cervix, the prostate, etc.). In addition, plastic applicators are not as mechanically robust as titanium applicators, thereby increasing the risk that the applicator may break during insertion and result in complications to the treatment procedure.

Recently, there has been developed "applicator libraries", such as BrachyVision™ v8.9 (available from Varian Medical Systems, Charlottesville, Va., USA). These applicator libraries store files containing characteristics of brachytherapy applicators, including geometric dimensions of various applicator configurations. In a treatment procedure, the applicator library files may be imported to a treatment data set and used to reconstruct a three-dimensional model of the physical applicator being used in the procedure. This may done by identifying a number of relevant points on the physical applicator with a three-dimensional imaging, and then registering the identified points with corresponding points in the stored library file. In this way, a model of the applicator may be generated showing its orientation within the treatment region. A further discussion of applicator libraries, and applicator commissioning, is provided by T. P. Hellebust, et al., Recommendations from Gynecological (GYN) GEC-ESTRO Working Group: considerations and pitfalls in commissioning and applicator reconstruction in 3D image-based treatment planning of cervix cancer brachytherapy, Radiotherapy and oncology: journal of the European Society for Therapeutic Radiology and Oncology 96, 153-160 (2010).

Even with the availability of applicator libraries however, there persist difficulties in attempting to use titanium applicators for brachytherapy procedures. In particular, though the precise dimensions of a titanium applicator may be recorded in a library file and imported into a clinical setting, complications arise in attempting to accurately register the imported dimensions from the library file with the dimensions of the physical applicator. This is due to the generation of susceptibility artifacts by the titanium material during MR imaging, which obscure the image and introduce inaccuracies in attempting to identify relevant points on the physical applicator for registration with the library file. Thus, performance of a brachytherapy procedure with a titanium applicator and a corresponding applicator library file normally requires the use of multiple imaging modalities (e.g., a combination of CT and MR imaging)—with a first imaging modality being used to reconstruct three-dimensional models (e.g., CT imaging modality), and a second imaging modality being used to guide insertion and placement of the applicator (e.g., MR imaging modality. This use of multiple imaging modalities complicates the procedure, increases the time and expense for performing the procedure, and continues to subject healthy tissues to ionizing radiation (e.g., through CT imaging).

SUMMARY OF THE INVENTION

The present application provides a novel marker-flange for MRI-guided brachytherapy. The marker-flange is configured to be received on, and affixed to, the external surface of a tandem in a brachytherapy applicator. The marker-flange includes a hollow chamber that holds an MR imaging responsive marker agent, and one or more ports for injecting and extracting a marker agent to and from the hollow chamber.

The marker-flange is provided with a configuration making it suitable for use as a cervical flange (i.e., a cervical stopper) with the tandem of an intracavitary brachytherapy applicator (e.g., a tandem-and-ovoid or tandem-and-ring applicator). In another example, the marker-flange is provided with a configuration making it suitable for use as a cervical sleeve. In yet another example, the marker-flange is provided with a configuration making it suitable for use as the "ring" structure in a tandem-and-ring applicator.

The marker agent contained within the hollow chamber of the marker-flange is an MR imaging responsive liquid marker material that generates MR image signal intensities sufficient to overcome susceptibility artifacts generated by titanium materials when subjected to MR imaging. In this manner, the combination of the external marker-flange with the marker agent provides clearly defined images with improved geometric accuracies, thereby facilitating the identification of relevant points on a physical brachytherapy applicator, and the registration of those points with corresponding points in an applicator library file.

The combination of the marker-flange and marker agent, with the improved signal intensities and geometric accuracies, thus facilitates the use of titanium applicators while also achieving increased reconstruction and dosimetry accuracies—while further enabling the procedure to be performed with only an MR imaging modality (thereby obviating the need for a CT imaging modality). The marker-flange and marker agent combination can also provide these same benefits when used with plastic applicators.

The marker-flange, with a marker agent therein, may be configured for a one-time use. Alternatively, the marker-flange may be configured for sterilization and refilling (enabling the removal and replacement of a marker agent) so as to permit repeated uses.

Both the foregoing general description and the following detailed description are exemplary and explanatory only and are intended to provide further explanation of the invention as claimed. The accompanying drawings provide a further understanding of the invention; are incorporated in and constitute part of this specification; illustrate several embodiments of the invention; and, together with the description, serve to explain the principles of the invention.

DESCRIPTION OF THE DRAWINGS

FIG. 4A shows exemplary dimensions of a marker flange for use with a titanium tandem applicator; and FIG. 4B shows exemplary dimensions of a marker flange for use with a plastic tandem applicator.

FIGS. 5A-5C show phantoms that were used in quantifying the signal intensities of MR imaging responsive marker agents. FIG. 5A shows a marker-flange phantom; FIG. 5B shows a tandem-and-ring brachytherapy applicator phantom; and FIG. 5C shows an interstitial needle phantom.

FIG. 8A shows the images used in a first step of globally registering images of the marker-flange phantom of FIG. 5A. FIG. 8B shows the images used in a second step of finely registering images of the marker-flanges.

FIG. 9A shows measurements taken from a coronal view; and FIG. 9B shows measurements taken from a sagittal view.

FIG. 15A shows a partial cross-section of the marker-flange in a sagittal view (with a radiation source wire received in the source pathway cavity, and projecting from the cross-section), and FIG. 15B shows a cross-section of the marker-flange in a transverse view (prior to loading a radiation source wire into the source pathway cavity).

DETAILED DESCRIPTION OF THE INVENTION

The following examples are intended to illustrate but not to limit the invention.

Marker-Flange

Figure 1:
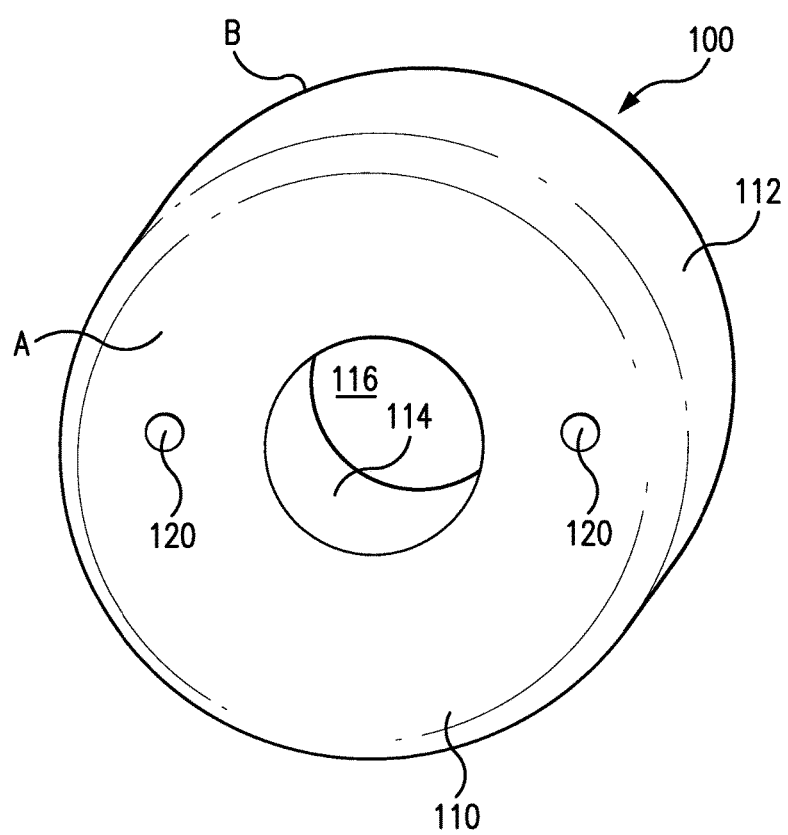
FIG. 1 shows a perspective front view of a marker-flange.
Figure 2:
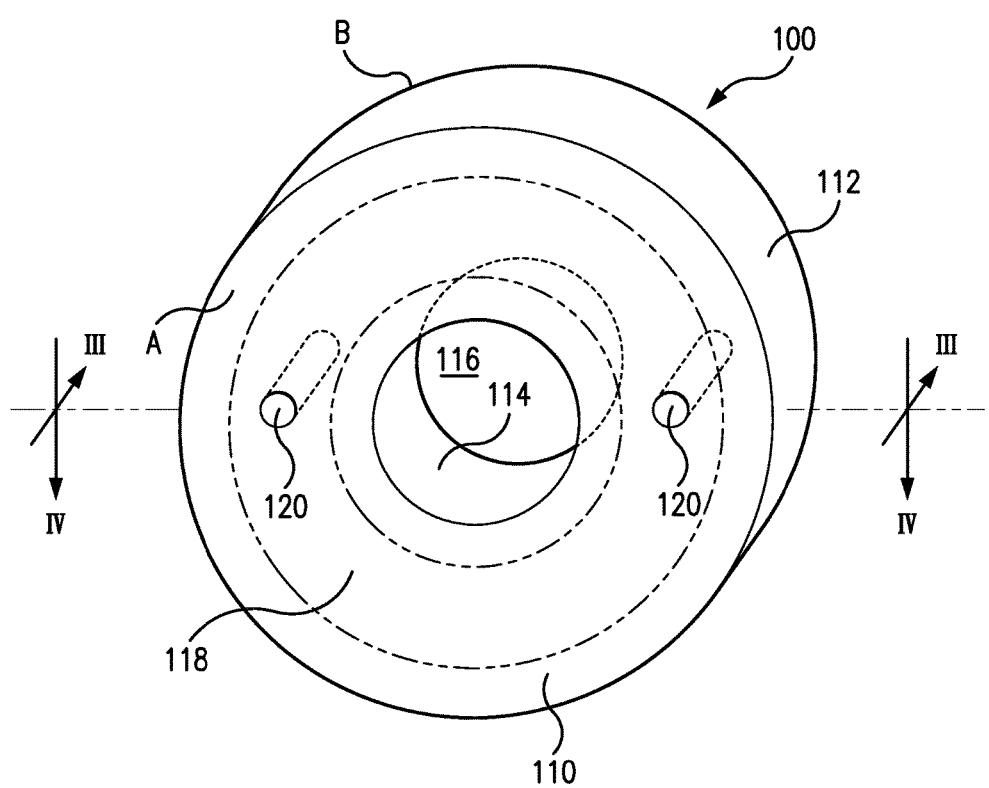
FIG. 2 shows another view of the marker-flange of FIG. 1, with hidden lines showing a hollow chamber for receiving a marker agent.
Figure 3:
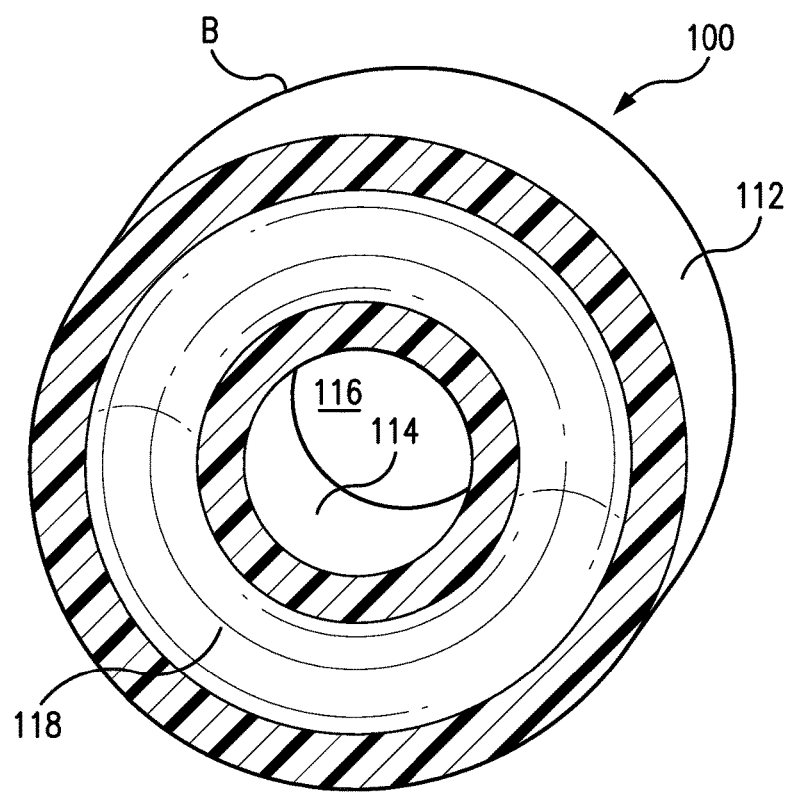
FIG. 3 shows a perspective cross-sectional view of the marker flange of FIG. 2, as seen along line III-III.
Figure 9A:
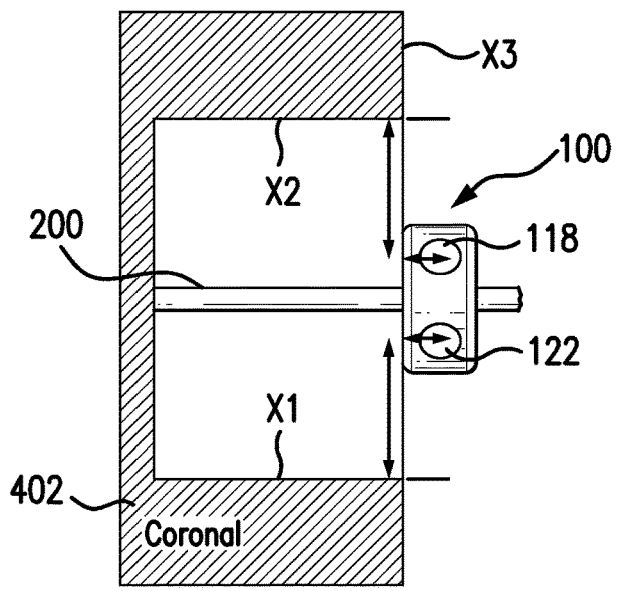
FIGS. 9A and 9B show reference walls and measurements taken from images of the marker-flange and marker agent combination in the phantom of FIG. 5A, for use in assessing geometric accuracies.
Figure 9B:
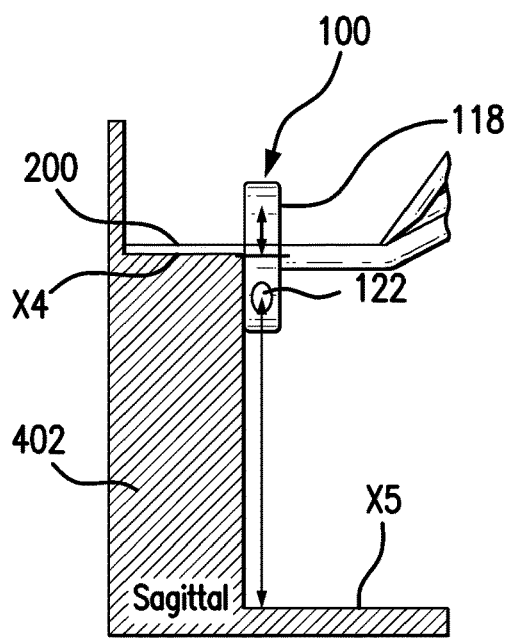

FIGS. 1-3 show one example of a marker-flange 100. The marker-flange includes a flange body 110 having a first face "A" and a second face "B". An outer wall 112 of the flange body 110 extends between the faces A/B. An inner wall 114 defines a cavity 116 that extends through the flange body 110. A hollow chamber 118 is arranged within the volume of the flange body 110 between the outer wall 112 and the inner wall 114. The hollow chamber 118 receives an MR imaging responsive marker material 122 (FIGS. 9A and 9B). The marker-flange 100 includes one or more ports 120, arranged on at least one of the faces A/B, which communicate with the hollow chamber 118.

The flange body 110 may be formed as a solid mold, with the hollow chamber 118 and the ports 120 formed as spatial voids within the otherwise solid mold. Alternatively, the flange body 110 may be formed as a hollow body, from two separately molded halves, with the hollow chamber 118 formed as a separate circular lumen that is inserted between the two halves of the flange body 110 during assembly. When forming a separate lumen body for the hollow chamber 118, the ports 120 may be formed as projections on the lumen body and then joined in a liquid-tight connection with cavities formed on an opposing face A/B of flange body 110.

The flange body 110 is formed from a biocompatible material which is MR imaging compatible to the extent that it will not interfere with the generation of MR image signals from an MR image responsive marker agent contained within the hollow chamber 118. The flange body can be made out of plastic material such as polyethelene. Examples of suitable materials for forming the flange body 110 include polysulfone, acetal, carbon fiber, polytetrafluoroethylene, fluorinated ethylene propylene, polytetrafluoroethylene-perfluoroalkyl vinyl ether copolymer, polyvinyl chloride, polypropylene, polyethelene, polyethylene terephthalate, broad fluoride, and similar biocompatible plastics. If the marker-flange 100 is desired for repeated uses, then the flange body 110 may be formed from a material suitable for repeated sterilization procedures, such as acetal which is feasible for repeated steam sterilization. However, alternative sterilization procedures may also be used, such as cold sterilization when the hollow chamber 118 contains a liquid or gel type MRI marker agent 122.

As shown in the example of FIG. 1, the first and second faces A/B may be formed with planar surfaces. Alternatively, one or both of the faces A/B may be formed with shaped faces that may include concave, convex, and wave-like contours. When used as a cervical flange, the use of a shaped surface on a face of the flange body may facilitate orientation of the marker-flange 100 flush against the cervix with the cavity 116 aligned with the cervical OS. Independent of the chosen surface shape (planar or contoured), the first and second faces A/B may be formed with a smooth surface texture so as to minimize irritation to any tissues that come into contact with the marker-flange 100.

Figure 10:
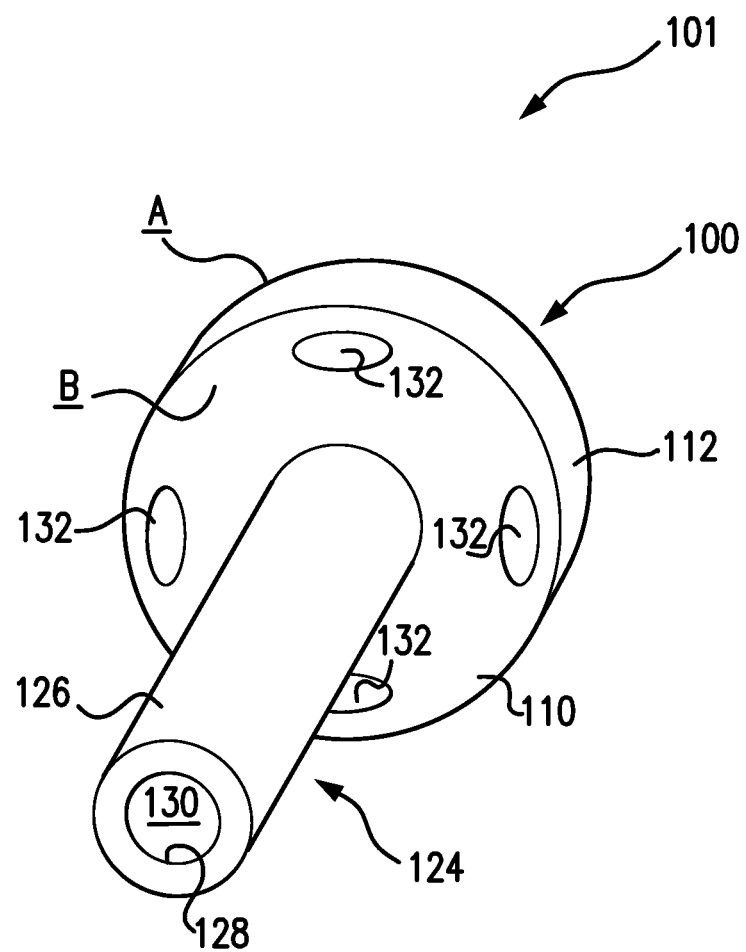
FIG. 10 shows a perspective view of a marker-flange integrated in a cervical sleeve.
Figure 11:
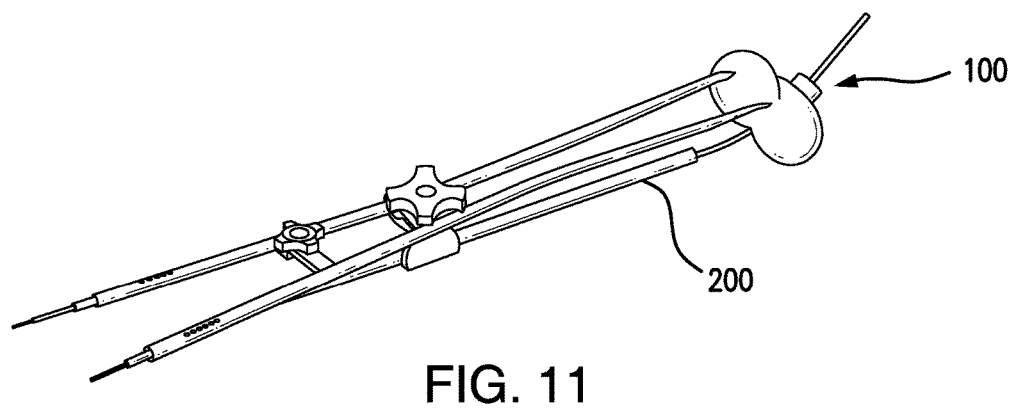
FIG. 11 shows a perspective view of a tandem-and-ovoid applicator, with a marker-flange affixed to the tandem applicator.

In another example shown in FIG. 10, the marker-flange 100 may be integrated into a cervical sleeve 101, such as a Smit Sleeve (available from Varian Medical Systems). In particular, the marker-flange 100 may include a shaft 124 that projects from one of the faces A/B. The shaft 124 may include an outer surface 126, and an inner surface 128. The inner surface 128 defines a channel 130 that communicates with the cavity 116 of the flange body 110, and which shares the same dimensional features (e.g., diameter, circumferential shape, etc.). The flange body 110 of the cervical sleeve 101 may include a plurality of channels 132 extending through the flange body in the axial direction, from the first face A to the second face B. These channels 132 are arranged at a radial position on the flange body 110 so as not to interfere with the hollow chamber 118 and the MR imaging of a marker agent 122 contained therein. In one example the channels 132 are arranged at radial distances within a boundary defined by the inner circumference of the hollow chamber 118. In another example, the channels 132 are arranged at radial distances outside a boundary defined by the outer circumference of the hollow chamber 118. The channels 132 are suitably dimensioned to permit passage of a surgical suturing needle and thread, so as to allow the cervical sleeve to be sutured to the cervix while the shaft 124 is inserted in the cervical OS. For example, the channels 132 may be formed with diameters similar to those used in a Smit Sleeve, such as a diameter in the range of 1.9 mm to 2 mm.

Figure 13A:
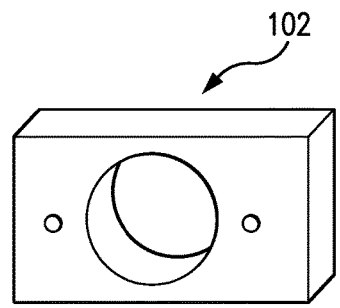
FIGS. 13A-13F show perspective views of exemplary marker-flanges.
Figure 13B:
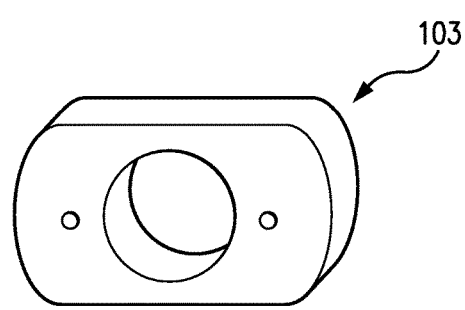
Figure 13C:
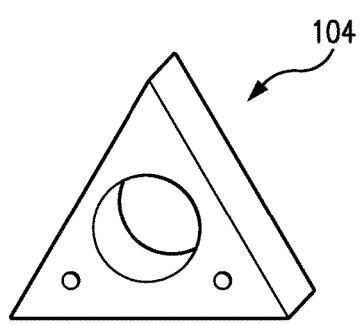
Figure 13D:
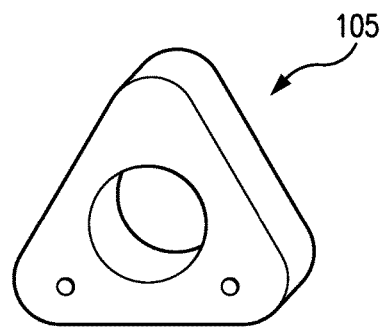
Figure 13E:
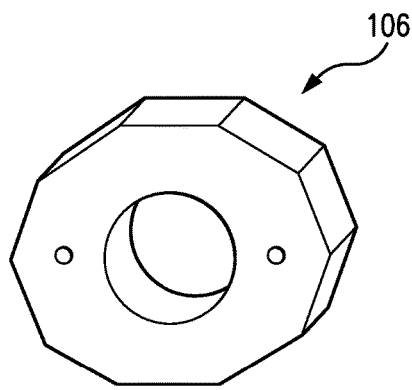
Figure 13F:
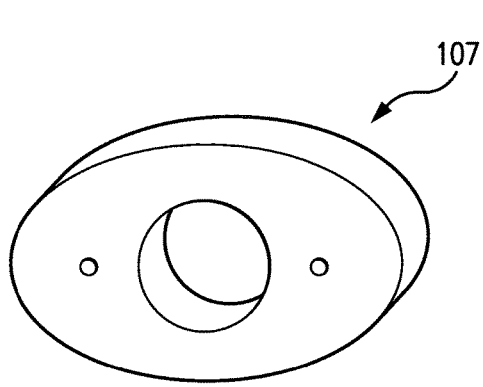

FIGS. 13A-13F show further examples of the marker-flange. FIG. 13A shows a marker-flange 102, which is constructed with a rectangular shape. FIG. 13B shows a marker-flange 103, which is constructed with a generally rectangular shape having arcuate sides. FIG. 13C shows a marker-flange 104, which is constructed with a triangular shape. FIG. 13D shows a marker-flange 105, which is constructed with a generally triangular shape having arcuate corners. FIG. 13E shows a marker-flange 106, which is constructed with a decahedron shape. FIG. 13F shows a marker-flange 107, which is constructed with an oval shape. Though not shown in these views, each of the marker-flanges 102-107 may include a shaft (such as the shaft 124), and through-channels (such as the channels 132), to thereby incorporate the marker-flange into a cervical sleeve.

In the example shown in FIGS. 1-3, the outer wall 112 and the inner wall 114 are both formed with a constant cross-sectional perimeter, such that both the outer diameter and the inner diameter of the marker-flange are constant along its axial length. The inner wall 114 defines the cavity 116. As shown in the example of FIGS. 1-4, the inner wall 114 is formed at a central region of the flange body 110, and is concentric and parallel with the outer wall 112. The cavity 116 extends entirely through the flange body 110, from the first face A to the second face B. The inner wall 114, and thus the cavity 116, is configured with suitable dimensions to receive the tandem of a brachytherapy applicator.

In another example, the outer wall 112 may be formed with a non-constant cross-sectional perimeter, such that the marker-flange 100 is provided with a contoured outer wall 112. A contoured shape for the outer wall 112 may include a tapered shape that decreases in width from one end to the other. Another contoured shape may include an hourglass shape, having an increased width at the proximal and distal ends and a decreased width in a mid-region therebetween. A further contoured shape may include a ribbed shape with a series of protuberances, or wave-like peaks and troughs, arranged along a length of the outer wall 112. The use of a contoured outer wall 112, such as the tapered and hourglass shapes, may facilitate a compact construction of a tandem-and-ovoid brachytherapy applicator by permitting the marker-flange 100 to closely conform to the curved portions of the ovoids. Also, a contoured shape such as the hourglass shape or the ribbed shape may provide a gripping region on the flange body to facilitate extraction of the flange marker 100, such as when the flange marker is integrated in a cervical sleeve 101.

As shown in FIGS. 1-4, the inner wall 114 is formed with a cylindrical circumference having a constant cross-sectional perimeter along its length so as to receive a cylindrical tandem. The flange body 110 may be made of a relatively compressible material, with the diameter of the circumferential wall 114 made to substantially correspond with the outer diameter of the tandem, such that the cavity 116 provides a press-fit connection with an inserted tandem by the flange body 110 compressing (i.e., the cavity 116 expanding) upon insertion of the tandem. Alternatively, the inner wall 114 may be formed with a circumferential hourglass shape along its axial length, such that the cavity 116 is provided with a larger diameter at its openings at faces A/B (larger than the outer diameter of the intended tandem), and a smaller diameter at an intermediate region. With such an hourglass shape, the larger diameter openings of the cavity 116 will facilitate insertion of the tandem, while the smaller diameter region provides a press-fit connection with the tandem.

The inner wall 114 and the cavity 116 may also be configured for reception of tandem applicators that have non-cylindrical cross-sections (e.g., oval, triangular, rectangular and other polyhedron cross-sections). Independent of the shapes chosen, both the outer wall 112 and the inner wall 114 may also include beveled edges extending between the walls and the faces A/B.

In examples where the hollow chamber 118 is formed as a lumen body (separate from two halves of a hollow flange body 110), the material used to form the lumen body may be a similar material as that used for forming the flange body 110. The ports 120 communicate with the hollow chamber 118, and are at least partially filled with a sealing agent in a sufficient volume to provide a liquid tight seal between the hollow chamber 118 and an external environment outside the flange body 110. A suitable sealing agent will be biocompatible, and will be sufficiently elastic so as to retain a liquid-tight seal between the hollow chamber 118 and the environment external to the marker-flange 100 after having been penetrated by a syringe needle (e.g., a self-resealing liquid tight seal). Examples of suitable materials for a sealing agent include silicone caulk, acetal, polyethylene, and polysulfone. In examples where the marker-flange 100 is desired for repeated uses, the sealing agent is formed from a material suitable for repeated sterilization procedures, such as acetal and polysulfone. Again, sterilization procedures for the marker-flange 100 may include steam sterilization and cold sterilization.

Figure 14A:
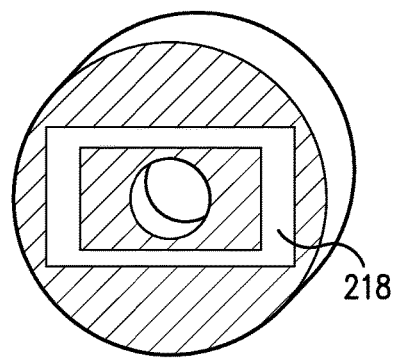
FIGS. 14A-14F show perspective cross-sectional views of marker flanges with exemplary hollow chambers.
Figure 14B:
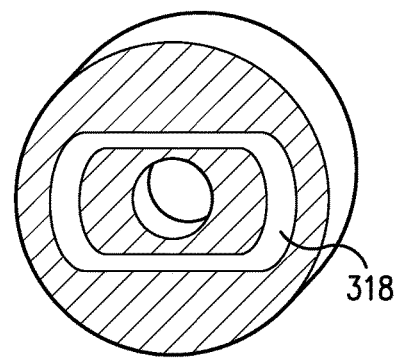
Figure 14C:
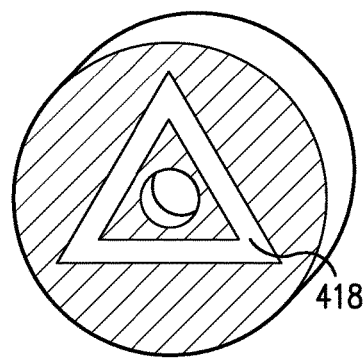
Figure 14D:
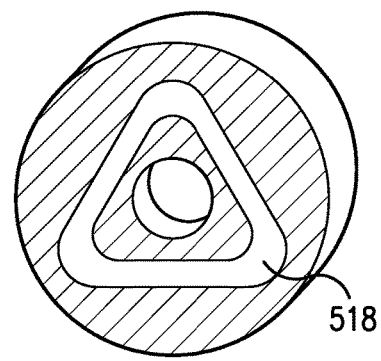
Figure 14E:
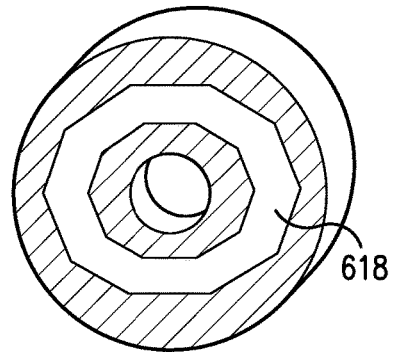
Figure 14F:
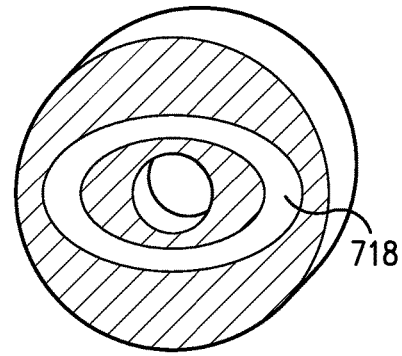

In the Example shown in FIGS. 1-4, marker-flange 100 is constructed with a hollow chamber 118 that is formed with a circular shape, thereby mimicking the outer profile of flange body 110. However, the hollow chamber 118 is not limited to a circular shape, and may be formed with other shapes as desired (e.g., triangular, rectangular, hexagonal, and other polyhedrons). FIGS. 14A-14F show further examples of the hollow chamber. FIG. 14A shows a hollow chamber 218, which is formed with a rectangular shape. FIG. 14B shows a hollow chamber 318, which is formed with a generally rectangular shape having arcuate sides. FIG. 14C shows a hollow chamber 418, which is formed with a triangular shape. FIG. 14D shows a hollow chamber 518, which is formed with a generally triangular shape having arcuate corners. FIG. 14E shows a hollow chamber 618, which is formed with a decahedron shape. FIG. 14F shows a hollow chamber 718, which is formed with an oval shape. In particular, the use of non-circular shapes for the hollow chamber 118, and in particular shapes having select symmetrical axes, may facilitate identification and reconstruction of both the marker flange shape and orientation during MR imaging. In one example the hollow chamber 118 may be formed in an isosceles triangular shape, such that the orientation of the base angles and the vertex angle in the isosceles triangle may be used as reference points for both the marker position and orientation, as well as the position and orientation of a brachytherapy applicator on which the marker-flange 100 is affixed. In examples where the hollow chamber 118 is formed with a shape other than circular, the flange body 110 may have a cylindrical shape, or may likewise be configured with a shape that mimics the shape of the hollow chamber 118.

One or more ports 120 may be arranged on only one of the faces A/B, or both of the faces A/B. In examples where the marker-flange 100 is provided with a shaped face A/B for contacting the cervix, the one or more ports 120 may be formed on the opposite face so as to avoid complications in forming a liquid-tight seal on the shaped surface. In examples where the marker-flange 100 is configured as a cervical sleeve 101 (as shown in FIG. 10) the one or more ports 120 may be formed on the opposite face from the shaft 124 so as to permit access to the ports 120 without interference from the protruding shaft 124.

Again, in one example, the ports 120 are at least partially filled with a sealing agent in a sufficient volume to provide a liquid tight seal between the hollow chamber 118 and an external environment outside the flange body 110. The sealing agent in this example is sufficiently elastic so as to retain a liquid-tight seal between the hollow chamber 118 and the environment external to the marker-flange 100 after having been penetrated by a syringe needle (e.g., a self-resealing liquid tight seal). In another example, the ports 120 themselves may be formed of a material that is sufficiently elastic to exhibit a self-resealing, liquid tight, characteristic. In this alternative example, the marker-flange 100 may be formed without providing a sealing agent within the ports 120.

Marker-Flange Examples

Figure 4A:
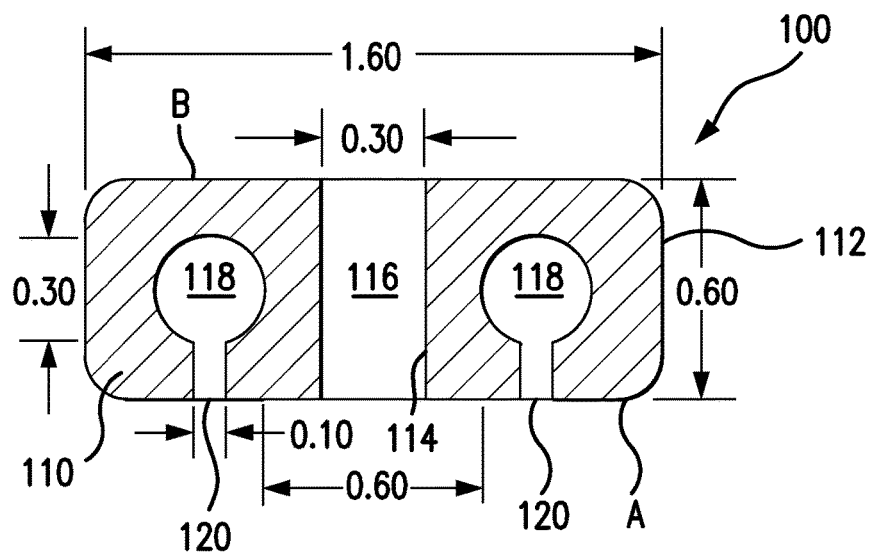
FIGS. 4A and 4B show two top plan cross-sectional views of the marker-flange shown in FIG. 2, as seen along line IV-IV.
Figure 4B:
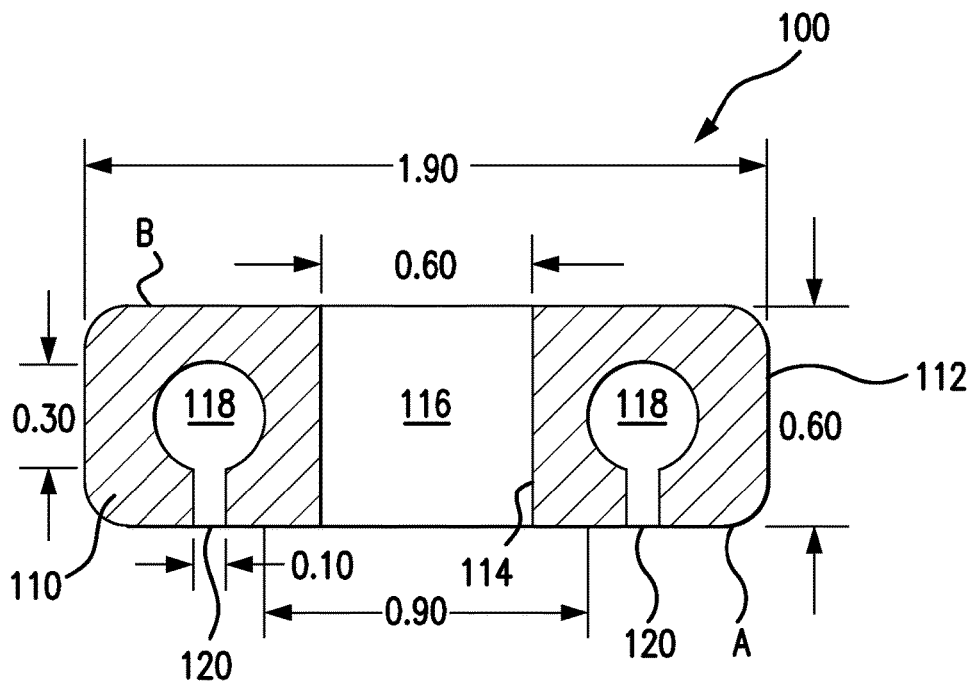

FIGS. 4A and 4B show examples of marker-flanges 100, with exemplary dimensions as may be used for a titanium tandem applicator (FIG. 4A) and a plastic tandem application (FIG. 4B). The dimensions shown in FIGS. 4A and 4B are in centimeters. It is noted that these measurements are merely exemplary, and are provided to aid in a comparison between the requirements of titanium applicators and plastic applicators. It is thus appreciated that the dimensions of the marker-flange 100, including the diameter of the inner wall 114 (and the cavity 116), may be modified as necessary to receive a desired tandem applicator.

The example shown in FIG. 4A presents a circular marker-flange 100 that is configured for use with a titanium tandem applicator. The outer wall 112 has a diameter of 1.6 cm, while the inner wall 114 (and the cavity 116) has a diameter of 0.3 cm. The hollow chamber 118 is formed in the shape of a torus, with the torus-cavity itself having a circular cross-section of 0.3 cm, and a diameter of approximately 0.6 cm, as measured from the inner circumference of the torus-cavity (e.g., the hole through the torus-shape). The marker-flange in this example is constructed with an outer wall 112 having an axial length of 0.6 cm, and ports 120 measuring 0.1 cm in diameter.

The example shown in FIG. 4B presents a circular marker-flange 100 that is configured for use with a plastic tandem applicator. The outer wall 112 has a diameter of 1.9 cm, while the inner wall 114 (and the cavity 116) has a diameter of 0.6 cm. The hollow chamber 118 is formed in the shape of a torus, with the torus-cavity itself having a circular cross-section of 0.3 cm, and a diameter of approximately 0.9 cm, as measured from the inner circumference of the torus-cavity (e.g., the hole through the torus-shape). The marker-flange in this example is also constructed with an outer wall 112 having an axial length of 0.6 cm, and ports 120 measuring 0.1 cm in diameter.

As can be seen from a comparison of FIGS. 4A and 4B, marker-flanges 100 for titanium and plastic tandem applicators may be constructed with substantially the same dimensions, with the exception that marker-flanges for plastic applicators must account for the larger diameter of the plastic applicators as compared to the smaller diameter of titanium applicators. On average, plastic tandem applicators have diameters measuring 6-7 mm, while titanium applicators have diameters measuring 3-3.2 mm. Thus, a marker-flange for a plastic applicator will be required to have a cavity 116 that is approximately twice the size as that needed for a titanium applicator. This increased diameter of the cavity 116 likewise requires an increase to the overall width of the marker-flange 100 (increasing the outer diameter from 1.6 cm to 1.9 cm), as well as an increase in the overall volume of the hollow chamber 118 (due to an increased diameter of the hole through the torus-shape from approximately 0.6 cm to approximately 0.9 cm).

Based on the differences in dimensions, marker-flanges 100 for use with titanium applicators may be produced with lesser quantities of raw materials for both the flange body 110 and the marker agent 122, thereby decreasing production costs. In particular, it is expected that the volume of an MR responsive marker agent 122 needed to fill the hollow chamber 118 for a marker-flange constructed for a plastic applicator will be approximately 133% (an additional $\frac{1}{3}^{rd}$) of the volume needed to fill the hollow chamber 118 of a marker-flange constructed for a the titanium applicator. For example, the marker-flange in FIG. 4A is expected to require approximately 0.1999 cc's of a marker agent 122 to be entirely filled, while the marker-flange of FIG. 4B is expected to require approximately 0.2665 cc's of a marker agent 122 to be entirely filled.

It is noted that the measurements and dimensions in the foregoing examples of FIGS. 4A and 4B are mere exemplary, and that the marker flange 100 may be constructed with other suitable dimensions as desired. For example, the titanium marker-flange of FIG. 4A may be constructed with an outer wall 112 having a larger diameter, such as one within the range of 1.6 cm to 2 cm; and with the inner wall 114 (and cavity 116) also having a larger diameter, such as one within the range of 3 cm to 0.35 cm.

Marker-Flange Ring

Figure 12:
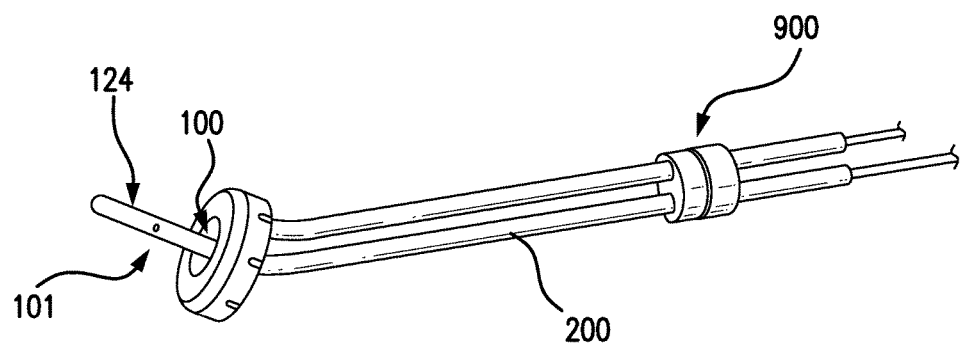
FIG. 12 shows a perspective view of a tandem-and-ring applicator, with a marker-flange integrated in a cervical sleeve that is received on the tandem applicator.
Figure 15A:
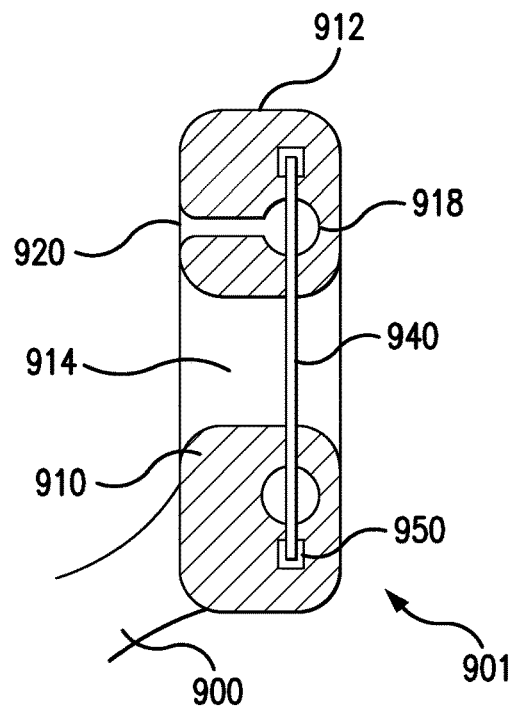
FIGS. 15A and 15B show a marker-flange integrated in a tandem-and-ring applicator.
Figure 15B:
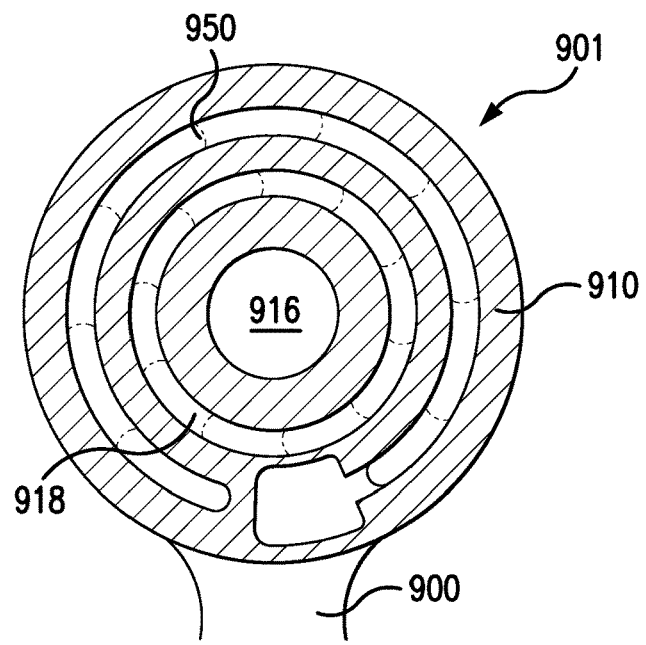

In yet another example, the marker-flange may be constructed integrally with a tandem-and-ring applicator as the "ring" portion of the applicator assembly. An example of a tandem-and-ring applicator 900 is shown in FIG. 12, and an example of a marker-flange 901 for incorporation with in such an assembly is shown in FIGS. 15A-15B. The marker-flange 901 is formed integrally with the tandem-and-ring applicator body 900, and includes a hollow chamber 918 that is formed in the flange body 910 between the outer wall 912 and the inner wall 914. At least one port 920 is provided on an outer face of the marker-flange 901 to facilitate the introduction of a marker agent 122 into the hollow chamber 918. The hollow chamber 918 may be pre-filled with a marker agent 122 during manufacturing of the marker-flange 901, with the port 920 sealed thereafter. Alternatively, the marker-flange 901 may be constructed with the hollow chamber 918 left empty, and the port 920 may be at least partially filled with a resealing agent which forms a liquid tight seal for the hollow chamber 918, while also permitting the later introduction of a marker agent 122 into the hollow chamber without compromising the liquid tight seal. As another alternative, the ports 120 themselves may be formed of a material that is sufficiently elastic to exhibit a self-resealing, liquid tight, characteristic, such that a sealing agent is not needed within the ports 120.

A particular feature of the marker-flange 901 is that the flange body 910 also includes a source pathway cavity 950, which is configured to receive a radiation source 940 during brachytherapy procedures. As such, the hollow chamber 918 is formed in the flange body 910 in a manner to compliment the arrangement of the source pathway cavity 950, and also to serve as a reference point for the location of the source pathway cavity 950 during reconstruction imaging. In addition, it is not necessary that the inner wall 914 (and cavity 916) of the marker-flange 901 be constructed with a diameter that is configured to achieve a press-fit connection with a tandem applicator. In particular, in the marker flange 901, the flange body 910 is supported by its integrated construction with the tandem-and-ring applicator 900. Accordingly, it is not necessary that the marker-flange be constructed with a cavity 916 that enables it to be affixes to the outer surface of a tandem applicator. Instead, the cavity 916 is constructed with a diameter sufficiently larger to enable the insertion and retraction of a tandem applicator therethrough, without any interference by contacting the inner wall 914. As such, it is possible to construct a single marker-flange 901 with a cavity 916 having sufficient dimensions that will enable it to be selectively used with either titanium tandem applicators or plastic tandem applicators.

Marker Agents

The hollow chamber 118 contains a marker agent 122 that is MR imaging responsive in that it is capable of generating a signal that is viewable with an MR imaging modality. The marker agent 122 may be injected into the hollow chamber 118 during manufacture, prior to delivery to an end user (e.g., a clinical procedure setting). Alternatively, the marker-flange 100 may be manufactured and delivered to an end user without a marker agent 122 contained in the hollow chamber 118, and an end user may inject a desired marker agent 122 into the hollow chamber 118 through the ports 120 prior to use in a clinical procedure. Due to the liquid-tight resealing character of the sealing agent in the ports 120, injection of a marker agent 122 through the ports 120 in this manner will not compromise the liquid-tight seal of the hollow chamber 118.

In testing there was observed a volume-effect for the MR imaging responsive marker agents 122, at least when contained and imaged within a plastic material. In particular, a catheter having an inner diameter of 0.1 cm and an outer diameter of 0.2 cm was inserted into the plastic ring of a tandem-and-ring brachytherapy applicator and imaged with an MR imaging modality. It was found that MR imaging of the ring (with the 0.1 cm/0.2 cm diameter catheter) did not result in any discernible images of the marker agent contained therein. The same procedure was then repeated with a larger catheter having an inner diameter of 0.2 cm and an outer diameter of 0.3 cm. It was found that MR imaging of the second ring (with the 0.2 cm/0.3 cm diameter catheter) successfully produced images of the marker agent contained therein. Thus, without being bound by theory and/or simulation, it is believed that there is a volume-effect for the marker agents 122 and it is therefore recommended that the marker-flange 100 be constructed with a hollow chamber 118 having a cross-sectional area of 0.2 to 0.3 cm. In this regard, it is also recommended that, in use, a sufficient volume of marker agent 122 be injected into the hollow chamber 118 to substantially fill the chamber so as to provide a suitable cross-section of the marker agent 122 for MR imaging.

Examples of MR imaging responsive marker agents 122 for use with the marker-flange 100 include: saline; Conray®-60 (an iothalamate meglumine composition available from Mallinckrodt Inc., St. Louis, Mo. USA); $CuSO_4$ (1.5 g/L); liquid Vitamin E; fish oil; 1% Agarose Gel (1 g agarose powder/100 mL distilled water); and C4 (a cobalt-chloride complex contrast; $CoCl2$: Glycine=4:1). The C4 marker agent is synthesized using anhydrous cobalt (II) chloride and glycine [$H_2N(CH_2)CO_2H$] reactants, which are dissolved in deionized water stirred at 60° C., followed by slow water evaporation yielding crystals of the synthesized compound. The crystals are then dissolved in deionized water stirred at 60° C. in the amount of 0.3-10% by weight.

The preferred marker agent 122 for use with the marker-flange 100 may vary based upon the imaging modality to be used in the procedure. For example, marker agents that yield favorable signals when imaged with a T1-weighted MR imaging modality (3.0 Tesla, with 1 mm slice thickness—hereafter "T1MRI") may prove unfavorable when imaged with a T2-weighted MR imaging modality (3.0 Tesla, with 3 mm slice thickness—hereafter "T2MRI"), and vice-versa.

Comparative Examples

Figure 5C:
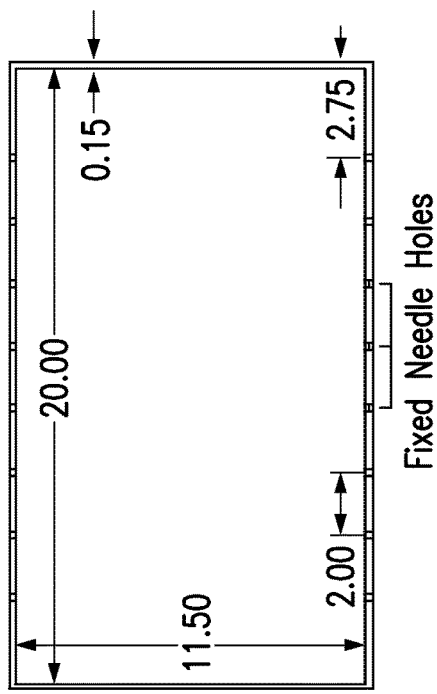
Figure 5C:
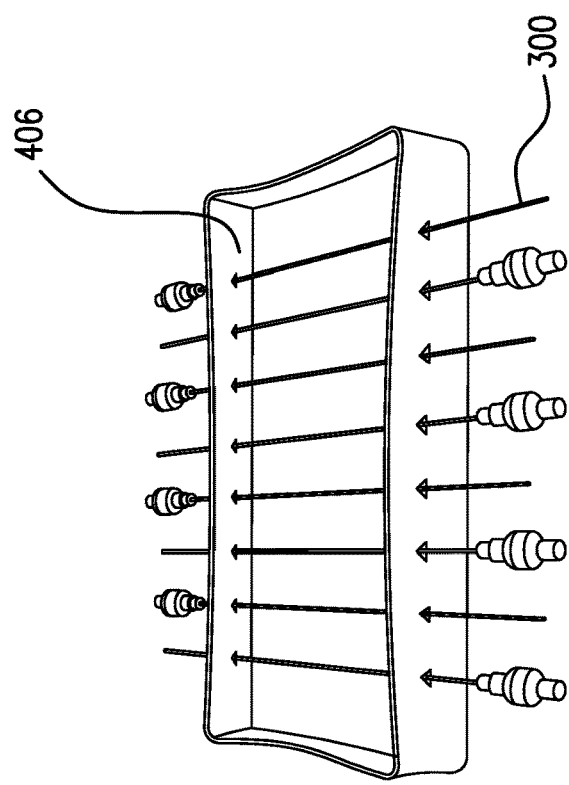

Signal intensities and geometric accuracies for the foregoing marker agents 122 were quantified through tests performed with the three phantoms shown in FIGS. 5A-5C.
Phantoms FIG. 5A shows a phantom 402 used for imaging marker-flanges 100, with the marker agents 122 contained in the hollow chamber 118 and a titanium tandem 200 inserted in the cavity 116. FIG. 5B shows a phantom 404 used for imaging a tandem-and-ring applicator 900 (for gynecological HDR brachytherapy) having a plastic tandem applicator 200, with imaging dummy-marker catheters containing the marker agents 122 inserted in the plastic tandem applicator. FIG. 5C shows a phantom 406 used for imaging interstitial flexi-needles 300 containing a marker agent 122. The dimensions shown in FIGS. 5A-5C are in centimeters.

The marker-flange phantom 402, shown in FIG. 5A, was developed to evaluate the signal quality of the marker-flanges 100 with the marker agents 122. The phantom 402 was a 5 L plastic phantom with 1500 ml of 3% agarose gel filling only the area of interest around the marker-flanges 100. The phantom 402 was designed to simultaneously test three marker-flanges 100 affixed to three separate titanium tandems 200 (available from Varian Medical Systems). Four plastic inserts aligned all three marker-flanges 100 in the same superior-to-inferior and anterior-to-posterior positions. Three guide holes were drilled to ensure that the titanium tandems 200 were aligned with the plastic inserts.

The tandem-and-ring phantom 404, shown in FIG. 5B, was developed in accordance with specifications set forth by Y. Kim, et al., Evaluation of Artifacts and Distortions of Titanium Applicators on 3.0-Tesla MRI: Feasibility of Titanium Applicators in MRI-Guided Brachytherapy for Gynecological Cancer, int. J. Radiat. Oncol. Biol. Phys. 2011; 80:947-955. The phantom was developed to suspend an applicator and to provide a reference for quantifying the image distortion and artifacts. Four different reference rods were designed to be located as a function of the distance from a tandem. The phantom 404 was designed for the tandem-and-ring to be positioned in intrinsic brachytherapy-eye-view (i.e. the scanning orientation of axial images is orthogonal to the axis of the intrauterine tandem). In addition, quality assurance (QA) procedures for a brachytherapy treatment planning system using three-dimensional (3D) images were also accounted for. The phantom 404 was a 5 L plastic phantom filled with 4000 ml of 3% agarose gel. The plastic tandem 200 of the tandem-and-ring applicator 900 was submerged in the 3% agarose gel and repeatedly scanned with seven dummy-marker catheters having inner and outer diameters measuring 1.87 mm and 2.86 mm respectively. The seven dummy-marker catheters were each filled with one of the marker agents 122 and sealed with hot glue to prevent leakage and limit evaporation of the marker agent.

The interstitial needle phantom 406, shown in FIG. 5C, was filled with 400 ml of 3% agarose gel. Seven separate flexi-needles 300 (available from Best Medical International Inc., Springfield, Va., USA), having inner and outer diameters measuring 1.45 mm and 1.98 mm respectively, were each filled with one of the marker agents 122 and sealed. The flexi-needles 300 were fed through the entire phantom 406 so that neither end of the flexi-needles was submerged in the agarose gel in order to ensure that agarose gel did not leak into the flexi-needles.

Marker-Agent Signal Intensities

In all of the phantoms 402, 404 and 406, 3% agarose gel (3 g agarose powder/100 ml distilled water) was used to simulate human tissue. A Siemens MAGNETOM Trio® 3T MR scanner (available from Siemens Medical Systems, Erlangen, Germany), with a body/spine array coil, was used to obtain high resolution 3.0 Tesla MR images. The MR imaging was performed according to the protocol set forth by Y. Kim, et al., Int. J. Radiat. Oncol. Biol. Phys. 2011; 80:947-955. T2-weighted TSE (turbo-spin-echo) MRI (T2MRI) protocol consists of voxel size ($1.0 \times 1.0 \times 3.0$ mm$^3$), slice thickness 3 mm, bandwidth 651 Hz, TR (repetition time) 2000 ms, and TE (echo time) 0.95 ms. T1-weighted GRE (gradient echo sequence) MRI protocol includes voxel size $1.2 \times 0.9 \times 1.0$ mm$^3$, slice thickness 1.0 mm, Bandwidth 600 Hz, TR 3.33 ms, and TE 0.95 ms. Both T2- and T1-weighted MRI (T1MRI) are scanned in axial direction with 3D isotropic reconstruction. The MRI marker signal can be increased by modifying MRI scan parameters. To demonstrate that the invented marker-flange generates significant marker signals under clinical MRI scan protocol, the clinical MRI scan protocols were not changed. A Siemens Biograph® 40 PET/CT scanner (available from Siemens Medical Systems, Erlangen, Germany) was used to obtain CT images of the marker-flanges 100 in the phantom 402 for use as "gold standard" measurements in quantifying the geometrical accuracy of the MR imaging signals generated by the marker-flange and marker agent combinations. The CT imaging protocol was kept constant between the individual images, including a slice thickness of 0.6 mm for high resolution images. ImageJ software (available from National Institute of Health Image, Bethesda, Md., USA) was used for comparative image analysis.

Figure 6A:
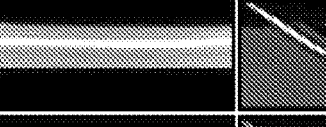
FIGS. 6A and 6B show MR generated images of the MR image responsive marker agents, as observed with the phantoms of FIGS. 5A-5C.
Figure 6B:

FIGS. 6A and 6B show MRI imaging results of several of the marker agents 122 imaged in the separate phantoms 402, 404 and 406. In particular, FIG. 6A shows images for the four highest-quality marker agents 122 imaged in the phantoms under a T1MRI modality; and FIG. 6B shows images for the four highest-quality marker agents 122 imaged in the phantoms under a T2MRI modality. In each figure, the left-most column lists the four marker agents 122 deemed to have the highest-quality, and the three right columns depict the MR images of phantom 406, phantom 404 and phantom 402 respectively.

Figure 7A:
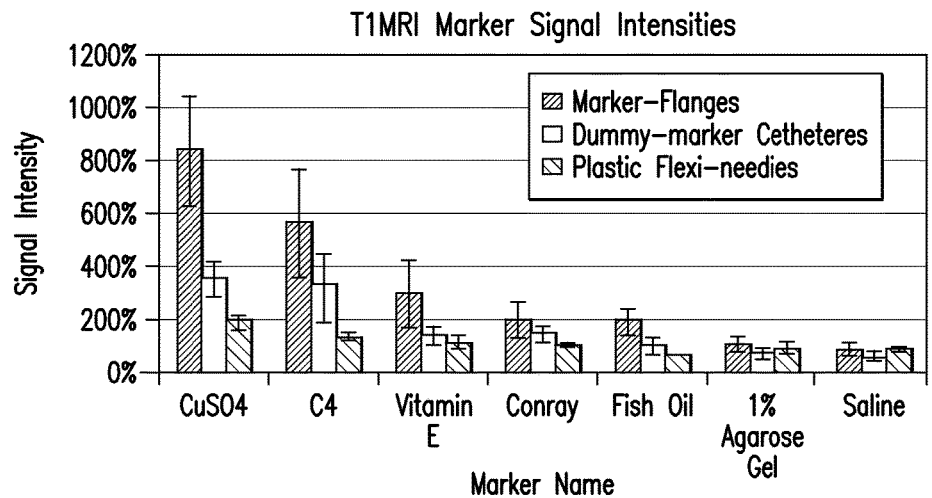
FIGS. 7A and 7B are bar charts showing the relative signal intensities of the MR image responsive marker agents, as compared with a background volume of 3% agarose gel.
Figure 7B:
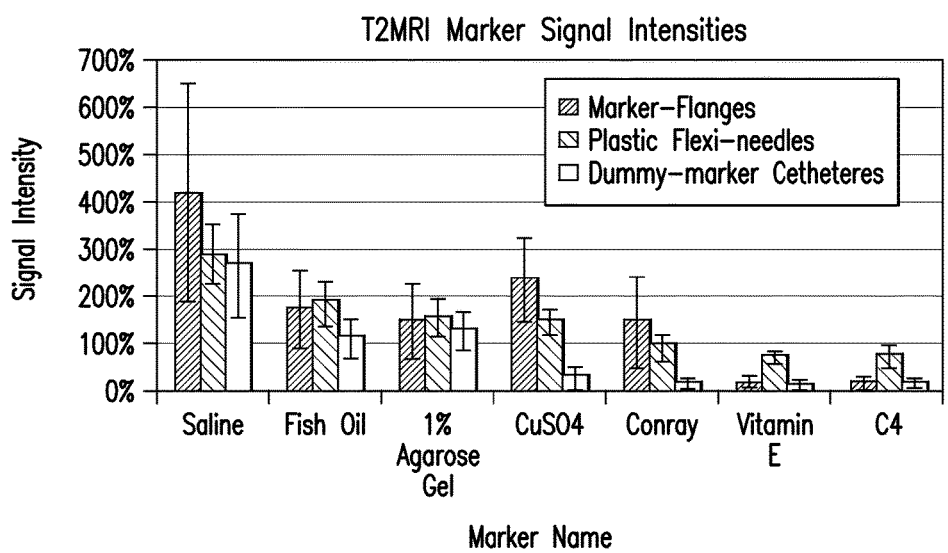

FIGS. 7A and 7B show signal intensities for the marker agents 122, expressed as percentages relative to the 3% agarose gel background (simulating human tissue). FIG. 7A shows calculated signal intensities for the marker agents 122 as imaged under a T1MRI modality; and FIG. 7B shows calculated signal intensities for the marker agents 122 as imaged under a T2MRI modality. In FIGS. 7A and 7B, the bar graphics above the individual marker agents 122 represent calculated average intensities of the respective marker agent, in the respective phantoms; and the "I-beam" graphics transposed over the bar graphics represent calculated standard deviations for the respective average intensities.

As can be seen in FIG. 7A, under the T1MRI imaging modality, the marker-flange 100 and marker agent 122 combinations (as obtained from phantom 402) repeatedly produced higher average signal intensities than those achieved with the dummy-marker catheters in the tandem-and-ring applicator 900 (phantom 404) and the interstitial flex-needles 300 (phantom 406). In particular, imaging of the marker-flange 100 under the T1MRI modality resulted in noticeably strong signal intensities for each of the $CuSO_4$, C4, liquid vitamin E, Conray-60®, and fish oil marker agents 122. The following signal intensities were recorded for the marker-flange 100 with the various marker agents 122, as obtained with the phantom 402 under the T1MRI modality:

$CuSO_4$—829±208%;
C4—558±203%;
Liquid vitamin E—288-131%;
Conray-60®—192±68%;
Fish oil—188±54%;
1% Agarose Gel—97±23%; and
Saline—81±21%;

As can be seen in FIG. 7B, under the T2MRI modality, the marker-flange 100 likewise produced stronger average signal intensities for each of the saline, $CuSO_4$, and Conray-60® marker agents. The following signal intensities were recorded for the marker-flange 100 with the various marker agents 122, as obtained with the phantom 402 under the T2MRI modality:

Saline—416±231%;
Fish Oil—174±81%;
1% Agarose Gel—148±80%;
$CuSO_4$—237±87%; and
Conray—147±95%.

Vitamin E and C4 showed lower than 100% signals

Marker-Flange Geometric Accuracy

The geometric accuracy of the marker-flange 100 and marker agent 122 combinations were assessed by comparing measurements taken from the centers of the marker agent 122 in images obtained with MR imaging modalities and with similar measurements taken from images obtained with an CT imaging modality.

Figure 8A:
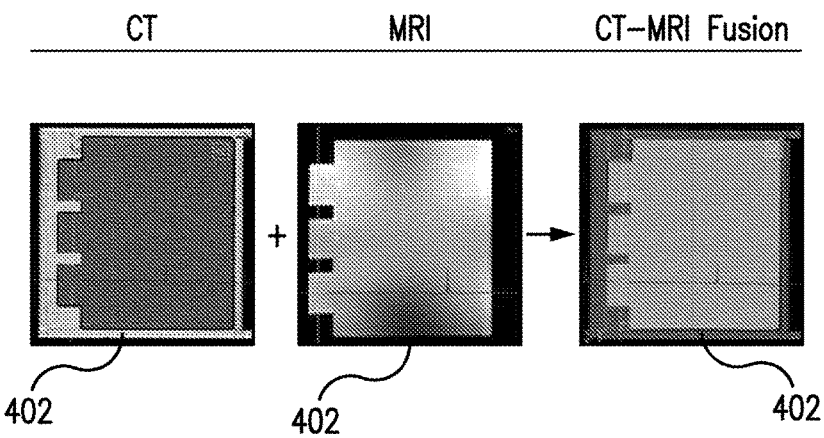
FIGS. 8A and 8B show the two step multi-imaging modality process that was used to assess the geometric accuracy of the marker-flange 100 with the MR imaging responsive marker agents in a CT-MRI Fusion imaging analysis.
Figure 8B:
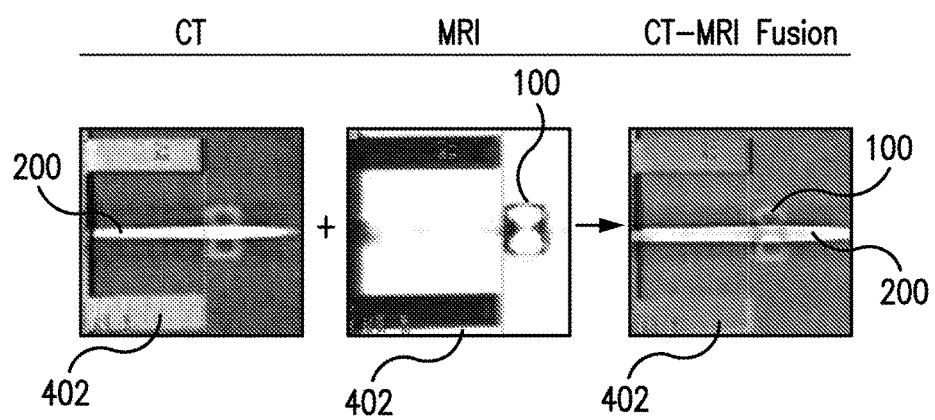

In particular, the phantom 402 was used to obtain images in both T1MRI and T2MRI modalities, as well as the CT imaging modality. The MR and CT images were then registered with one another in two steps using multi-imaging modality registration software Syngo® (available from Siemens Medical Systems). In step one, as shown in FIG. 8A, the phantom 402 was imaged with both the CT modality and the MR modality at a plane not intersecting either the marker-flange 100 or the titanium tandem 200. The CT and MR images were then globally registered using the walls and plastic inserts of the phantom 402. In step two, as shown in FIG. 8B, each individual marker-flange 100 was imaged with both the CT modality and the MR modality, and these images were finely registered with one another using the local plastic inserts adjacent the marker-flanges 100.

After the CT and MR images were registered, four distances were measured from center regions of the marker agent 122 to reference walls (X1, X2, and X3) in an MRI Coronal view (FIG. 9A). Two additional distances were measured from center regions of the marker agent 122 to reference walls (X4 and X5) in an MRI Sagittal view. These measurements were also made with in similar views obtains with a CT imaging modality. The differences (Δ) between measured distances on MRI and the measured distances on CT were recorded. The mean and standard deviation (SD) values of the differences (Δ) were calculated. These values, reflecting the geometric accuracy of the MRI signal for each marker-flange 100 and marker agent 122 combinations as compared to the "gold standards" of the CT images, are listed in Table 1.

TABLE 1

Geometric accuracy of the MRI signals obtained from each Marker-Flange

| | T1MRI | | T2MRI | |
| --- | --- | --- | --- | --- |
| MRI marker agent | Δ (mm) | SD (mm) | Δ (mm) | SD (mm) |
| Conray-60 | 0.70 | 0.77 | 2.17 | 0.42 |
| C4 | 1.95 | 0.11 | 1.93 | 1.32 |
| Saline | 0.77 | 0.25 | 1.59 | 0.96 |
| Fish oil | 1.06 | 0.71 | 1.60 | 2.21 |
| 1% Agarose gel | 0.67 | 0.67 | 2.66 | 1.11 |
| Vitamin E | 1.51 | 0.49 | 1.70 | 1.16 |
| $CuSO_4$ | 0.42 | 0.14 | 1.42 | 0.81 |

Abbreviations: T1MRI = T1-weighted MRI; T2MRI = T2-weighted MRI.
The 3-dimensional vector distances between MRI and CT datasets and phantom reference points are listed.

It is noted that the CT images used as the "gold standard" for comparison with the MRI images were taken at a slice thickness of 0.6 mm. Thus, the CT images provide a highly accurate geometrical reference for assessing the accuracy of the MRI images. In addition, it is noted that uncertainties caused from distortions and chemical shift artifacts were not separately measured; and that the values of Table 1 include any such uncertainties, along with any uncertainties induced by the registration algorithm and pixel size (0.4 mm) on the image registration software.

As can be seen from Table 1, under the T1MRI modality, the marker-flange 100 provided a geometric accuracy with an average difference (Δ) of less than 1 mm for each of the marker agents Conray®-60; saline; 1% agarose gel; and $CuSO_4$. The marker agent $CuSO_4$ showed the highest geometric accuracy under the T1MRI modality with a 3D MR image distortion of only 0.42±0.14 mm. It is noted that 0.5 mm is theoretically the smallest uncertainty when using a 1 mm slice thickness.

As can also be seen from Table 1, though less accurate than the T1MRI modality, each combination of the marker-flange 100 and marker agent 122 succeeded in achieving an average difference (Δ) of less than 3 mm under the T2MRI modality. Without wishing to be bound by theory and/or application, it is believed that these higher values under the T2MRI modality are due to the larger slice thickness (3 mm in T2MRI as compared to 1 mm in T1MRI).

Preferred Marker Agents

A preferred marker agent 122 will produce high-intensity signals while yielding high geometric accuracies. Thus, for three-dimensional reconstruction with a T1MRI modality, the marker agents $CuSO_4$, C4, and liquid vitamin E are preferred. Alternatively, for three-dimensional reconstruction performed with a T2MRI modality, the marker agents saline and $CuSO_4$ are preferred.

If the marker-flange 100 is desired for repeated uses, then it may also be preferred that the marker agent 122 is be minimally affected by evaporation and/or degradation so as to allow for better sustainability of the MRI signal intensity over time. It is noted that liquid vitamin E was found to be less effected by evaporation than $CuSO_4$, with $CuSO_4$ being observed to degrade in as a little as three months. Accordingly, preference may be given to using liquid vitamin E as a marker agent 122 (over $CuSO_4$) in favor of its longer stability. Alternatively, a reusable marker-flange 100 may employ a degradable marker agent 122, such as $CuSO_4$, with the marker agent being replenished on a regular schedule by extracting the degraded volume of the marker agent 122 from the marker flange and replacing it with a fresh volume of marker agent 122 via a port 120 in the flange body.

Methods of Use

The marker flange 100 may be received by an end user (e.g., a clinical treatment facility) with a suitable marker agent 122 contained in the hollow chamber 118. Alternatively, the marker-flange 100 may be received by an end user without any marker agent 122, and the end user may introduce a suitable marker agent 122 into the hollow chamber 118 prior to use. Introduction of the marker agent 122 may be achieved, with the use of a syringe, through the port 120.

Prior to initial use, the end user's applicator library should be updated to commission the marker-flange 100 and generate library files for use with the marker-flange. The commissioned library files for the marker-flange should include the geometric dimensions of the marker-flange 100 as well as relevant identifiable points on the marker-flange for use in registering the library file with corresponding points generated from imaging a physical marker-flange 100 affixed to a brachytherapy applicator.

Preferably, commissioning of the marker-flange 100 should include separate files for each variation of the marker-flange 100 (e.g., titanium marker flanges having a 1.6 cm width; plastic marker-flanges having a 1.9 cm width, and etc.). In addition to geometric dimensions of the marker-flange 100 itself, commissioning should also include geometric dimensions relating the location at which the marker-flange 100 will be affixed on an applicator with other relevant structures of the applicator (e.g., a distance from the affixed marker-flange location to a tandem tip; a distance from the affixed marker-flange location to an ovoid or ring structure; etc.). Commissioning should also include separate library files for each brachytherapy applicator (e.g., various tandem-and-ovoid applicators with a marker-flange; various tandem-and-ring applicators with a marker-flange; etc.), and may also include a separate file for each combination of an applicator, marker-flange 100, and marker agent 122.

When performing a brachytherapy procedure, the corresponding applicator library file for the chosen combination of a brachytherapy applicator, marker-flange 100 and marker agent 122 is selected. MR imaging is performed to identify relevant points on the marker-flange 100, and those point are registered with corresponding points stored in the applicator library file to reconstruct an accurate three-dimensional model of the brachytherapy applicator (and its orientation within the treatment region) based on the images of the marker-flange 100. The reconstructed model is then used to facilitate MRI-guided insertion and placement of the brachytherapy applicator in preparation for the delivery of a radiation source material to a target tissue.

In another example, the marker-flange 100 may be affixed on the brachytherapy applicator at a position to serve as a cervical flange. As a cervical flange the marker-flange 100 may be affixed to the outside surface of a tandem applicator and used to abut the cervix during insertion of the tandem into the cervical OS. In this manner, the cervical marker-flange 100 may be used to guide and limit the insertion distance of the tandem applicator into the uterus, thereby minimizing the possibility of causing harm the surrounding tissues (e.g., preventing perforation of the uterine wall from over-extension of the tandem).

In a further example, when configured as a cervical sleeve 101, the marker-flange 100 may again be affixed on the brachytherapy applicator at a position to serve as a cervical flange. However, as a cervical sleeve 101 the marker-flange 100 may facilitate brachytherapy treatments that will require multiple dose-delivery procedures. In particular, the integrated cervical sleeve 101 may be introduced into the vaginal cavity during an initial brachytherapy procedure, and the shaft 124 inserted into the cervical OS. The cervical sleeve 101 may then be sutured in place, using the channels 132 on the flange body 110 as anchoring structures, and the cervical sleeve may left in situ after completion of the initial brachytherapy procedure. Thereafter, in subsequent brachytherapy procedures, the cervical sleeve 101 (with the marker agent 122 contained therein) may be employed as a reference point in reconstructing a three-dimensional model of the treatment region and further facilitate an MRI-guided insertion of a brachytherapy applicator. When performing the subsequent dosing procedures, a separate marker-flange 100 may be affixed on the brachytherapy applicator to further assist in the three-dimensional reconstruction and MRI-guided insertion of the applicator itself.

In yet a further example, the marker-flange may be configured as a ring structure 901 integrated in a tandem-and-ring applicator 900. In such an instance, the marker-flange 901 may be used in a similar manner as contemplated in the previous methods (for marker-flanges generally). However, due to the proximity of the hollow chamber 918 to the source pathway cavity 950, the marker-flange 901 may also be used to achieve improved accuracy in the reconstruction of the source pathway within the ring structure of the tandem-and-ring applicator.

The inventive marker-flange 100 set forth herein, in combination with the marker agents 122, promotes the generation of strong MR image signal intensities with high geometric accuracies. In particular, the MR image signals generated by the marker-flange 100 have been found to overcome the susceptibility artifacts generated by titanium materials, thereby facilitating the use of titanium applicators in brachytherapy procedures with the use of only an MR imaging modality. In addition, the marker-flange 100 has been found to achieve improved geometric accuracies that are expected to improve geometric accuracies in the three-dimensional reconstruction of applicators, as well as improve the dose delivery accuracy of a radiation source. Furthermore, in addition to facilitating the use of titanium applicators, the inventive marker-flange 100 is expected to also improve reconstruction and dose delivery accuracies with plastic applicators.

To the extent necessary to understand or complete the disclosure of the present invention, all publications, patents, and patent applications mentioned herein are expressly incorporated by reference to the same extent as though each were individually so incorporated.

Having thus described exemplary embodiments of the present invention, it should be noted by those skilled in the art that the foregoing disclosures are exemplary only and that various other alternatives, adaptations, and modifications may be made within the scope of the present invention.

For example, although the foregoing examples are directed at a cylindrically shaped marker-flange 100, it is understood that the marker-flange 100 may be formed with any desired shape (e.g., conical; cubic; dodecahedron; etc.), and that certain shapes having select symmetrical axes may facilitate the MR imaging identification and three-dimensional reconstruction of the marker-flange. Additionally, although the marker-flange 100 has been disclosed relative to the foregoing marker agents 122, the marker-flange may also be used with other liquid marker agents, and may also be adapted for use with solid marker agents. Furthermore, although the examples in the foregoing disclosure are directed at brachytherapy procedures for the treatment of endometrial cancers, the marker-flange 100 may be adapted for use in other intracavitary brachytherapy procedures such as the treatment of prostate and esophageal cancers. In addition, ranges expressed in the disclosure are considered to include the endpoints of each range, all values in between the end points, and all intermediate ranges subsumed by the end points.

Accordingly, the present invention is not limited to the specific embodiments as illustrated herein, but is only limited by the following claims.

I claim:

1. A marker-flange for use with a brachytherapy applicator, comprising:
   a flange body having a first face and a second face, with a hollow chamber positioned in the flange body between the first and second faces;
   a cavity comprising a first cavity opening on the first face and a second cavity opening on the second face, the cavity extending through the flange body and dimensioned to receive a tandem in a brachytherapy applicator in a press-fit connection;
   a port comprising a port opening positioned on one of the first and second faces of the flange body, the port being configured to communicate with the hollow chamber; and
   a sealing agent contained within the port opening, the sealing agent providing an air-tight seal between the hollow chamber and an external environment outside the flange body.

2. The marker-flange of claim 1, further comprising:
   a marker agent contained within the hollow chamber.

3. The marker-flange of claim 2, wherein:
   the marker agent is a liquid, magnetic resonance (MR) imaging responsive marker agent.

4. The marker-flange of claim 3, wherein:
   the marker agent is chosen from the group consisting of: saline; an iothalamate meglumine composition; liquid vitamin E; fish oil; 1% Agarose Gel; and C4 cobalt-chloride complex.

5. The marker-flange of claim 1, wherein:
   the sealing agent contained in the port opening comprises an elastomeric material having a sufficient elasticity to exhibit a self-resealing characteristic after having been penetrated by a syringe.

6. The marker-flange of claim 1, wherein:
   the cavity is cylindrically shaped and has a diameter between 3.0 and 7.0 mm in a cross-section.

7. The marker-flange of claim 1, further comprising a shaft extending from one of the first and second faces of the flange body, wherein the shaft has a narrower width than the flange body.

8. The marker-flange of claim 7, wherein:
   the shaft includes a channel that communicates with the cavity in the flange body.

9. The marker-flange of claim 7, further comprising:
   channels formed in the flange body, the channels being dimensioned to receive a suture thread for suturing the flange body to the outer surface of a cervix.

10. A brachytherapy applicator, comprising:
    a marker flange comprising a flange body having a first face and a second face, with a hollow chamber positioned in the flange body between the first and second faces, the hollow chamber configured to receive and retain magnetic resonance (MR) imaging responsive marker agent; and
    a cavity extending through the flange body and dimensioned to receive a tandem in the brachytherapy applicator, without the outer surface of the tandem contacting a surface of the flange body that defines the cavity, wherein
    the brachytherapy applicator is a tandem-and-ring applicator, and the marker-flange is an integrated ring portion in the tandem-and-ring applicator, with one of the first and second faces of the flange body configured to abut a cervix upon use of the tandem-and-ring applicator with insertion of the tandem into a cervical OS.

11. The brachytherapy applicator of claim 10, wherein:
    the marker agent is a liquid marker agent.

12. The brachytherapy applicator of claim 11, wherein:
    the marker agent is chosen from the group consisting of: saline; an iothalamate meglumine composition; liquid vitamin E; fish oil; 1% Agarose Gel; and C4 cobalt-chloride complex.

13. The brachytherapy applicator of claim 10, wherein:
    the flange body is formed from an elastomeric material having a sufficient elasticity to exhibit a self-resealing characteristic after having been penetrated by a syringe.

14. The brachytherapy applicator of claim 10, wherein:
    the marker flange further comprises a port positioned on one of the first and second faces of the flange body, the port communicating with the hollow chamber and containing a sealing agent so as to provide an air-tight seal between the hollow chamber and an external environment outside the flange body.

15. The brachytherapy applicator of claim 14, wherein:
the sealing agent contained in the port is an elastomeric material having a sufficient elasticity to exhibit a self-resealing characteristic after having been penetrated by a syringe.

16. The bracytherapy applicator of claim 10, wherein the flange body further comprises a source pathway cavity for insertion of a radiation source into the flange body.

17. The brachytherapy applicator of claim 16, wherein the source pathway cavity and the hollow chamber extend around the flange body cavity on a common plane transverse to a central axis of the flange body cavity.

18. A method for performing a brachytherapy procedure, including:
introducing magnetic resonance (MR) imaging responsive marker agent into the hollow chamber of the marker-flange of claim 1; and
inserting a tandem of a brachytherapy applicator into the cavity of the marker-flange, so as to affix the marker-flange to an outside surface of the tandem.

19. The method for performing a brachytherapy procedure of claim 18, wherein:
the sealing agent contained in the port opening is composed of an elastomeric material having a sufficient elasticity to render it self-resealing after penetration by a syringe, and
introducing a marker agent into the hollow chamber includes using a syringe to inject a liquid marker agent through the port.

20. The method for performing a brachytherapy procedure of claim 18, wherein:
inserting a tandem into the cavity of the marker-flange includes affixing the marker-flange at a position on the tandem for use as a cervical flange for abutting a cervix upon the insertion of the tandem into a cervical os.

21. The method for performing a brachytherapy procedure of claim 18, wherein:
the marker-flange includes a shaft extending from one of the first and second faces of the flange body, with the shaft having a channel that communicates with the cavity of the flange body,
the marker-flange further includes channels formed in the flange body, the channels being dimensioned to receive a suture thread for suturing the flange body to the outer surface of a cervix,
inserting a tandem into the cavity of the marker-flange includes affixing the marker-flange at a position on the tandem for use as a cervical sleeve for abutting a cervix upon the insertion of the tandem into a cervical os; and
the method further includes inserting the shaft of the marker-flange into a cervical OS, and suturing the marker-flange to the cervix.

22. The method for performing a brachytherapy procedure of claim 18, wherein:
inserting a tandem into the cavity of the marker-flange includes inserting a titanium tandem into the cavity; and
the method further includes using three-dimensional imaging to guide the titanium tandem, with the marker flange affixed to an outside surface thereof, into an intracavitary treatment region,
wherein the three-dimensional imaging is performed using only an MR imaging modality.

* * * * *